United States Patent
Nicholson et al.

(10) Patent No.: US 9,487,612 B2
(45) Date of Patent: Nov. 8, 2016

(54) (METH)ACRYLOXY-CONTAINING TRISILOXANE, SILOXANE-CONTAINING POLYMERS AND BIOMEDICAL DEVICES THEREFROM

(71) Applicant: Momentive Performance Materials Inc., Waterford, NY (US)

(72) Inventors: John Nicholson, Ramsey, NJ (US); Ping Jiang, New City, NY (US); Vikram Kumar, Tarrytown, NY (US); Anubhav Saxena, Bangalore (IN); Umapathy Senthilkumar, Bangalore (IN); Eric Pohl, Mount Kisco, NY (US); Kendall Guyer, Bartlett, IL (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/765,878

(22) PCT Filed: Feb. 5, 2014

(86) PCT No.: PCT/US2014/014796
§ 371 (c)(1),
(2) Date: Aug. 5, 2015

(87) PCT Pub. No.: WO2014/123956
PCT Pub. Date: Aug. 14, 2014

(65) Prior Publication Data
US 2015/0368386 A1   Dec. 24, 2015

Related U.S. Application Data

(60) Provisional application No. 61/761,259, filed on Feb. 6, 2013.

(51) Int. Cl.
*G02B 1/04* (2006.01)
*C08F 230/08* (2006.01)
*C07F 7/08* (2006.01)
*C09D 143/04* (2006.01)
*C08K 5/5425* (2006.01)

(52) U.S. Cl.
CPC ........... *C08F 230/08* (2013.01); *C07F 7/0849* (2013.01); *C07F 7/0852* (2013.01); *C07F 7/0879* (2013.01); *C08K 5/5425* (2013.01); *C09D 143/04* (2013.01); *G02B 1/04* (2013.01); *G02B 1/043* (2013.01)

(58) Field of Classification Search
CPC ........................................................ G02B 1/043
See application file for complete search history.

(56) References Cited

U.S. PATENT DOCUMENTS

| | | |
|---|---|---|
| 3,408,429 A | 10/1968 | Wichterle |
| 3,496,254 A | 2/1970 | Wichterle |
| 4,084,459 A | 4/1978 | Clark |
| 4,197,266 A | 4/1980 | Clark et al. |
| 4,847,398 A | 7/1989 | Mehta et al. |
| 4,857,583 A | 8/1989 | Austin et al. |
| 5,159,096 A | 10/1992 | Austin et al. |
| 5,191,103 A | 3/1993 | Mehta et al. |
| 2015/0011671 A1* | 1/2015 | Saxena ............... C08L 83/14 523/107 |

FOREIGN PATENT DOCUMENTS

| | | |
|---|---|---|
| WO | 84/00763 A1 | 3/1984 |
| WO | 2013/142052 A2 | 9/2013 |
| WO | 2013/142055 A2 | 9/2013 |

OTHER PUBLICATIONS

Good RJ, Stromberg RR, editors. Surface and colloid science—Experimental methods, vol. 11. New York: Plenum Publishing; 1979. pp. 31-61.
Robert F. Fedors, Polymer Engineering and Science, Feb. 1974, vol. 14, No. 2.
International Search Report and Writteen Opinion dated Apr. 30, 2014.

* cited by examiner

*Primary Examiner* — Michael Pepitone
(74) *Attorney, Agent, or Firm* — Joseph S. Ostroff

(57) ABSTRACT

There is provided a trisiloxane having a 3-(meth)acryloxy-substituted (hydroxylcyclohexyl)ethyl group, useful in making water absorbing silicone-hydrogel films for biomedical devices, such as contact lens, and a process for producing these monomers. This invention also provides for copolymers made from the trisiloxane having a 3-(meth)acryloxy-substituted (hydroxylcyclohexyl)ethyl group described herein.

20 Claims, No Drawings

(METH)ACRYLOXY-CONTAINING TRISILOXANE, SILOXANE-CONTAINING POLYMERS AND BIOMEDICAL DEVICES THEREFROM

CROSS REFERENCE TO RELATED APPLICATIONS

The present application claims priority from U.S. Provisional Patent Application No. 61/761,259, filed on Feb. 6, 2013, which is incorporated by reference herein in its entirety.

FIELD OF THE INVENTION

The present invention provides for a trisiloxane containing a 3-(meth)acryloxy-substituted (hydroxylcyclohexyl) ethyl group, process for making same, and polymers and hydrogel compositions useful for the production of biomedical devices, especially contact lenses, therefrom.

BACKGROUND OF THE INVENTION

Contact lenses with the object of continuous wear for a long term are made of silicone rubber prepared from polydimethyl siloxanes. High water content contact lenses are made of poly-N-vinylpyrrolidone polymers. Since the silicone rubber contact lenses are very water-repellent and greatly different from the cornea in thermal properties such as thermal conductivity and thermal diffusivity, they give a foreign body sensation, particularly a burning sensation despite having oxygen permeability. Contact lenses made from silicone rubber are uncomfortable to wear. Further, the silicone rubber is soft and elastic, making it difficult to conduct precise mechanical treatments such as cutting, grinding, and polishing. Many attempts for making the surface of silicone rubber lenses hydrophilic have been undertaken, but no completely satisfactory contact lens has been developed. Since the high water content contact lenses contain about 60% to about 80% by weight of water, they have the disadvantages that they are weaker in quality of material than low water content contact lenses, are easily contaminated with inorganic and organic compounds in tears which penetrate and accumulate into the lenses during the use, and are bad in maintenance of lens contour due to the evaporation of water during the use and, therefore, the refractive power thereof easily changes.

Conventional hydrogel materials made from 2-hydroxyethylmethacrylate (HEMA) have poor oxygen permeability and poor oxygen transport to the eye through the absorbed water molecules. Water has low oxygen permeability. Contact lenses made from 2-hydroxyethylmethacrylate monomers are slowly dehydrated and the amount of oxygen transported to the cornea is reduced upon exposure to atmospheric air for longer periods. Eye irritation, redness and other corneal complications can result and hence restrict use of the lenses to limited periods of wear.

Silicone-hydrogel films are used to make extended wear soft contact lenses due to their high oxygen permeability, flexibility, comfort and reduced corneal complications. Silicone-hydrogels have overcome some of the obstacles for long periods of wear beyond conventional hydrogels because these silicone-hydrogels make comfortable soft contact lenses with higher oxygen permeability than the conventional hydrogel materials. However, these silicone-hydrogels have deficiencies. For example, many of the silicone-hydrogels used linear blocks of dimethylpolysiloxanes to improve oxygen permeability. It is known that polysiloxanes, which contain α,ω-terminal unsaturated groups bonded through divalent hydrocarbon groups or amino-containing hydrocarbon groups (heterocarbon groups), have been used in preparing soft, contact lenses. Lower molecular weight unsaturated siloxane-polyether copolymers with the α, ω-divinylpolysiloxanes have also been used in combination with unsaturated polysiloxane-polyether copolymers and a compatibilizing additive. These polymers contain linear hydrophobic dimethylpolysiloxane chains, which form hydrophobic regions within the polymer and may cause corneal complications or difficulties in conducting precise mechanical treatments.

Methacryloxypropyltris-(trimethylsiloxy)silane monomers have been used to prepare silicone-containing hydrogels. The (meth)acryloxypropyltris-(trimethylsiloxy)silane is hydrophobic and is used in preparing polyurethane-silicone polymers. These polyurethane-silicone polymers contain blocks of hydrophobic silicone. Contact lenses made from these polymers may cause eye discomfort because of the hydrophobic regions within the polymer.

Silicone-hydrogels are typically made from acrylate or methacrylate functionalized silicone monomer that are polymerized with hydrophilic monomers, such as hydroxyethyl methacrylate (HEMA), N-vinylpyrrolidone (NVP) and other monomers such as methyl methacrylic acid (MA), and dimethylacrylamide (DMA), in the presence of crosslinker and free radical or photoinitiators. Crosslinking agents generally have two or more reactive functional groups at different sites of the molecule. Typically, these sites contain polymerizable ethylenic unsaturation groups. During polymerization to form the silicone-hydrogel, they form a covalent bond with two different polymer chains and form a stable three-dimensional network to improve the strength of the polymer. Crosslinking agents conventionally used in contact lenses include ethylene glycol dimethacrylate and trimethyloylpropane trimethacrylate. Other useful crosslinking agents include diethyleneglycol dimethacrylate, bisphenol A dimethacrylate, diglycidyl bisphenol A dimethacrylate and dimethacrylate-terminated polyethylene glycol and reactive linear polyether modified silicones. The oxygen permeability of these silicone-hydrogels is affected by the chemical structure of the acrylate or methacrylate functionalized silicone monomer and choice of the other monomers containing reactive carbon-carbon double bonds that are used in preparing the crosslinked polymer.

Silicone-hydrogel contact lens materials are typically made using either hydrophobic mono-functional silicone monomers or multi-functional hydrophilic silicone monomers followed by secondary surface treatment. Mono-functional silicone monomers are often used in the contact lens industry over multi-functional silicone monomers since the latter lead to increased rigidity in the lenses made therefrom. The known mono-functional silicone monomers, however, may have deficiencies. For example, monofunctional siloxane-polyether (meth)acrylates are susceptible to air oxidation. Monofunctional (meth)acryloxy functional siloxanes that contain 1,4-substition the (meth)acryloxy group to the siloxane group on a six-member ring, such as for example, (meth)acrylic acid 2-hydroxy-4-[2-bis-(trimethylsiloxy) methylsilanyl-ethyl]-cyclohexyl ester, form highly ordered copolymers which may inhibit the permeability of oxygen through the silicone-hydrogel.

Although the state of the art for soft contact lenses has been improving, silicone-based materials still possess major shortfalls, like sub-optimal surface wettability and oxygen permeability, and the need for compatibilizers in preparing the polymer. In an effort to overcome these drawbacks, current state of the art technology uses either expensive secondary surface treatments called "plasma oxidation", or internal wetting agents. These approaches may decrease oxygen permeability or require the use of compatibilizers, which adds costs during the manufacturing process.

Hence, there remains a need for hydrophilic silicone monomers with inherently advantageous wettability, stability to air oxidation, high oxygen permeability and high solubility in the other reactive monomers used to make the polymer without the need for compatibilizers. The trisiloxane containing a 3-(meth)acryloxy-substituted (hydroxylcyclohexyl)ethyl group of the present invention can be used to make contact lenses without the drawbacks of poor wettability, oxidative instability, less than optimal oxygen permeability, expensive surface treatments and processing costs associated with using compatibilizer necessary with the silicone containing materials of the present art.

BRIEF SUMMARY

The present invention discloses new mono-acrylate or methacrylate functionalized trisiloxane monomers having the structure of Formula (I):

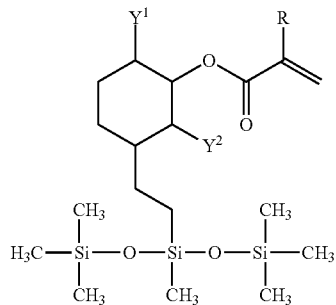

(I)

wherein R is hydrogen or methyl; $Y^1$ is hydrogen or hydroxyl (—OH); and $Y^2$ is hydrogen or hydroxyl (—OH), with the proviso that at least one $Y^1$ or $Y^2$ is a hydroxyl group. These functionalized silicone monomers are useful for making polymers and water-absorbing, oxygen-permeable silicone-hydrogel films containing the same that can be fashioned into biomedical devices, especially extended wear soft contact lenses.

The present invention also describes a process for producing trisiloxane containing a 3-(meth)acryloxy-substituted (hydroxylcyclohexyl)ethyl group monomers and polymers made by reacting the trisiloxane monomers having the general Formula (I) with hydrophilic monomers containing an activated carbon-carbon double bond.

DETAILED DESCRIPTION OF THE INVENTION

In accordance with the present invention, a (meth)acryloxy-containing trisiloxane having the general Formula (I):

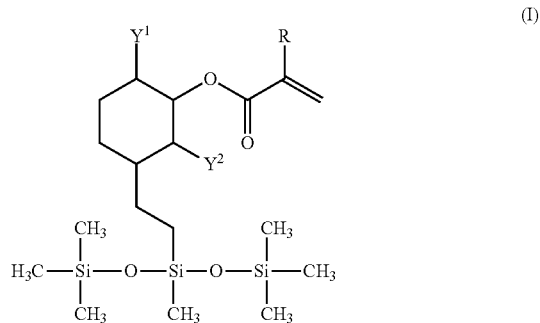

(I)

wherein R is hydrogen or methyl; $Y^1$ is hydrogen or hydroxyl (—OH); and $Y^2$ is hydrogen or hydroxyl (—OH), with the proviso that at least one $Y^1$ or $Y^2$ is a hydroxyl group. More specifically, mono-acrylate or methacrylate functionalized trisiloxane monomers are provided wherein R is hydrogen, $Y^1$ is a hydroxyl group and $Y^2$ is hydrogen, or mono-acrylate or methacrylate functionalized trisiloxane monomers are provided wherein R is hydrogen, $Y^1$ is hydrogen and $Y^2$ is a hydroxyl group.

In one embodiment, the stereochemistry of the (meth)acryloxy group to the bis-(trimethylsiloxy)methylsilanylethyl group is trans-1,3-substitution of the cyclohexyl group. Although not to be held to any theory, the trans-1,3-substitution of the cyclohexyl group is believed to introduce more randomness (entropy) into the polymer containing the monomer of the present invention, thereby introducing a large free volume and better oxygen permeability.

Representative and non-limiting examples of the trisiloxanes containing a 3-(meth)acryloxy-substituted (hydroxycyclohexyl)ethyl group include acrylic acid 2-hydroxy-5-[2-bis-(trimethylsiloxy)methylsilanyl-ethyl]-cyclohexyl ester, methacrylic acid 2-hydroxy-5-[2-bis-(trimethylsiloxy)methylsilanyl-ethyl]-cyclohexyl ester, acrylic acid 2-hydroxy-3-[2-bis-(trimethylsiloxy)methylsilanyl-ethyl]-cyclohexyl ester, and methacrylic acid 2-hydroxy-3-[2-bis-(trimethylsiloxy)-methylsilanyl-ethyl]-cyclohexyl ester, and mixtures thereof. Preferably, the representative and non-limiting examples of the trisiloxanes containing a 3-(meth)acryloxy-substituted (hydroxycyclohexyl)ethyl group include acrylic acid trans-2-hydroxy-trans-5-[2-bis-trimethylsiloxy)methylsilanyl-ethyl]-cyclohexyl ester, methacrylic acid trans-2-hydroxyl-trans-5-[2-bis-(timethylsiloxy)methylsilanyl-ethyl]-cyclohexyl ester, acrylic acid trans-2-hydroxy-trans-3-[2-bis-(trimethylsiloxy)-methylsilanyl-ethyl]-cyclohexyl ester, and methacrylic acid trans-2-hydroxy-trans-3-[2-bis-(trimethylsiloxy)methylsilanyl-ethyl]-cyclohexyl ester, and mixtures thereof. More preferably, the representative and non-limiting examples of trisiloxanes containing a 3-(meth)acryloxy-substituted (hydroxycyclohexyl)ethyl group include acrylic acid trans-2-hydroxy-trans-5-[2-bis-(trimethylsiloxy)methylsilanyl-ethyl]-cyclohexyl ester and methacrylic acid trans-2-hydroxy-trans-5-[2-bis-(trimethylsiloxy)-methylsilanyl-ethyl]-cyclohexyl ester with the structure with the stereochemistry of Formula (II):

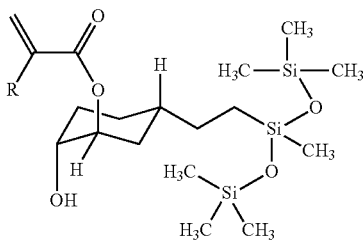

(II)

wherein R is hydrogen or methyl. In the chemical structure given by Formula (II), the carbon atom on the ring to which the (meth)acryloxy group is bonded is assigned the 1-position (C-1) on the ring. The (meth)acryloxy group is bonded to the C-1 carbon in an axial position of the cyclohexane ring. The hydroxyl group occupies the axial position on C-2 carbon atom of the cyclohexane ring. The stereochemistry of the hydroxyl group is trans relative to the (meth)acryloxy group. The 2-bis-(trimethylsiloxy)methylsilanyl-ethyl group occupies an equatorial position on C-5 carbon atom of the cyclohexane ring and is trans relative to the (meth)acryloxy group. The composition of acrylic acid trans-2-hydroxy-trans-5-[2-bis-(trimethylsiloxy)methylsilanyl-ethyl]-cyclohexyl ester is preferably greater than 85 weight percent, more preferably greater than 95 weight, based upon the total weight of the acrylic acid trans-2-hydroxy-trans-5-[2-bis-(trimethylsiloxy)methylsilanyl-ethyl]-cyclohexyl ester and the acrylic acid trans-2-hydroxy-cis-4-[2-bis-(trimethylsiloxy)methylsilanyl-ethyl]-cyclohexyl ester. The composition of methacrylic acid trans-2-hydroxy-trans-5-[2-bis-(trimethylsiloxy)methylsilanyl-ethyl]-cyclohexyl ester is preferably greater than 85 weight percent, more preferably greater than 95 weight, based upon the total weight of the methacrylic acid trans-2-hydroxy-trans-5-[2-bis-trimethylsiloxy)methylsilanyl-ethyl]-cyclohexyl ester and the methacrylic acid trans-2-hydroxy-cis-4-[2-bis-(trimethylsiloxy)methylsilanyl-ethyl]-cyclohexyl ester.

In another embodiment, the trisiloxanes containing a 3-(meth)acryloxy-substituted (hydroxycyclohexyl)ethyl group composition comprises from 40 to 99 weight percent acrylic acid trans-2-hydroxy-trans-5-[2-bis-(trimethylsiloxy)methylsilanyl-ethyl]-cyclohexyl ester and 1 to 60 weight percent of acrylic acid trans-2-hydroxy-cis-4-[2-bis-(trimethylsiloxy)methylsilanyl-ethyl]-cyclohexyl ester based upon the total weight of the two isomers, or from 40 to 99 weight percent methacrylic acid trans-2-hydroxy-trans-5-[2-bis-(trimethylsiloxy)methylsilanyl-ethyl]-cyclohexyl ester and 1 to 60 weight percent methacrylic acid trans-2-hydroxy-cis-4-[2-bis-(trimethylsiloxy)methylsilanyl-ethyl]-cyclohexyl ester, based upon the total weight of the two isomers.

The process for preparing trisiloxanes containing a 3-(meth)acryloxy-substituted (hydroxycyclohexyl)ethyl group having the general Formula (I) comprises:

(a) reacting a ethenyl-oxa-bicyclo[4.1.0]heptane with 1,1,1,2,3,3,3-heptamethyl-trisiloxane in the presence of a hydrosilylation catalyst; and (b) reacting the product of step (a) with (meth)acrylic acid to open the oxirane ring and provide for the trisiloxane containing a 3-(meth)acryloxy-substituted (hydroxycyclohexyl)ethyl group, optionally in the presence of an addition catalyst.

The preferred stereochemistry of the 3-ethenyl-7-oxa-bicyclo[4.1.0]heptane has the oxygen atom of the oxirane ring bonded to the 1 and 6-carbon atoms of the cyclohexyl group in the C-1 equatorial and C-6 axial positions and the vinyl group is bonded to the 3-carbon atom of the cyclohexyl ring in the equatorial position, and the 2-ethenyl-7-oxa-bicyclo[4.1.0]heptane and has the oxygen atom of the oxirane ring bonded to the 1 and 6-carbon atoms of the cyclohexyl group in the C-1 axial and C-6 equatorial positions and the vinyl group is bonded to the 2-carbon atom of the cyclohexyl ring in the equatorial position. These stereoisomers promote the axial attack of the (meth)acylate nucleophile on the epoxy ring and thereby promotes the 1,3-substitution of the cyclohexyl ring with the (meth)acryloxy group relative to the bis-(trimethylsiloxy)methylsilanyl-ethyl group.

Commercially available 3-enthenyl-7-oxa-bicyclo[4.1.0] heptane and experimentally produced 2-ethenyl-7-oxa-bicyclo[4.1.0]heptane are made from the epoxidation of 4-vinyl-cyclohexene and 2-vinyl-cyclohexene, respectively. The epoxidation of the more highly substituted carbon-carbon double bond can be achieved by treating alkene with peroxide-containing reagents, which donate a single oxygen atom. Typical peroxide reagents include hydrogen peroxide, peroxycarboxylic acids (generated in-situ or preformed), alkyl hydroperoxides and dimethyldioxirane. More specifically, the epoxidation agent is selected from the group consisting of perbenzoic acid, m-chloroperbenzoic acid, monoperphthalic acid and peracetic acid. These epoxdation agents allow for the isolation of the formed epoxide. The reaction may be carried out in an organic solvent solvent, such as chlorinated hydrocarbons, ethers or esters. Representative and non-limiting examples of the solvents include methylene chloride, chloroform, diethyl ether, tetrahydrofuran, and ethyl acetate.

The epoxidation reaction generates two stereoisomers of 3-ethenyl-7-oxa-bicyclo[4.1.0]heptane and two stereoisomers of 2-ethenyl-7-oxa-bicyclo[4.1.0]heptane. It is preferred that the stereoisomers of 3-ethenyl-7-oxa-bicyclo [4.1.0]heptane or stereoisomers of 2-ethenyl-7-oxa-bicyclo [4.1.0]heptane be separated from each other prior to the reaction with the 1,1,1,2,3,3,3-heptamethyl-trisiloxane. The stereoisomers can be separated by fraction distillation, preparative gas chromatography, preparative liquid chromatography or other methods commonly used in separating stereoisomers. Preferably, the stereoisomers are separated using fractional distillation of the mixture of stereoisomers at elevated temperatures and at subatmospheric, atmospheric or superatmospheric pressures. Most preferably, the stereoisomers are separated by fractional distillation using a rectification column having greater than 20 theoretical plates at atmospheric pressure and temperature ranging from 165° to 170° C.

The 3-ethenyl-7-oxa-bicyclo[4.1.0]heptane, which has the oxygen atom of the oxirane ring bonded to the 1 and 6-carbon atoms of the cyclohexyl group in the C-1 equatorial and C-6 axial positions and has the vinyl group bonded to the 3-carbon atom of the cyclohexyl ring in the equatorial position, is preferably greater than 85 weight percent, and more preferably greater than 95 weight percent, based upon the total weight of the two stereoisomers. Similarly, the 2-ethenyl-7-oxa-bicyclo[4.1.0]heptane, which has the oxygen atom of the oxirane ring bonded to the 1 and 6-carbon atoms of the cyclohexyl group in the C-1 axial and C-6 equatorial positions and has the vinyl group bonded to the 2-carbon atom of the cyclohexyl ring in the equatorial position is preferably greater than 85 weight percent, and more preferably greater than 95 weight percent, based upon the total weight of the two stereoisomers.

The 1,1,1,2,3,3,3-heptamethyl-trisiloxane may be prepared by a variety of methods, including hydrolysis and condensation of trimethylchorosilane and methyldichlorosilane followed by separation of the product or equilibration of hexamethyldisiloxane with a silanic silicone fluids and separation of the desired product using fractional distillation. Further purification, such as redistillation, is often used to prepare high purity 1,1,1,2,3,3,3-heptamethyl-trisiloxane (normal boiling point 142° C.), free of higher molecular weight oligomers and hexamethyldisiloxane.

The hydrosilylation reaction between 1,1,1,2,3,3,3-heptamethyl-trisiloxane and the ethenyl-oxa-bicyclo[4.1.0]heptane is conducted in the presence of a hydrosilylation catalyst, especially noble metal hydrosilylation catalysts. The catalysts include platinum, palladium, ruthenium, iridium and rhodiumas well as compounds containing these metals. These catalysts may be supported on activated carbon, aluminum oxide, ceramic materials and the like or in a colloidal suspension often formed in situ by the reduction of metal salts. Homogeneous catalysts are preferred, including chloroplatinic acid dissolved in ethanol, isopropanol or octanol and the platinum(0)-1,3-divinyl-1,1,3,3-tetramethyldisiloxane complex, known as Karstedt catalyst, dissolved in xylene or polydimethylsiloxane oils.

The catalyst is employed in a catalytic amount sufficient to induce and complete the hydrosilylation reaction. Specifically, the amount of catalyst is from 1 to 100 ppm metal catalysts based on the weight of the metal and the total weight of 1,1,1,2,3,3,3-heptamethyl-trisiloxane and the ethenyl-oxa-bicyclo[4.1.0]heptane. The hydrosilylation reaction may be conducted in a continuous process or a batch process wherein the reactants are introduced into a reactor and the temperature of the mixture adjusted to within the range of from 0° C. to 180° C., and more specifically from 20° C. to 120° C. Upon addition of the catalyst, the reaction is usually exothermic, peaking at a temperature of from 75° C. to 200° C. The reaction can be conducted in an inert atmosphere such as nitrogen.

The hydrosilylation reaction can be optionally conducted in the presence of promoters, as described in U.S. Pat. Nos. 4,847,398; 4,857,583; 5,191,103; or 5,159,096, relevant portions of which are incorporated herein by reference. These promoters include salts of carboxylic acids having Formula (III):

RCO$_2$M                                                      (III)

wherein:

M is hydrogen, alkali or alkaline earth metals, ammonium or phosphonium salts; and R represents a hydrogen or monovalent hydrocarbon group of from 1 to 20 carbon atoms. The preferred carboxylic acids are monocarboxylic acids containing from 3 to 20 carbon atoms. The carboxylic acid derived promoter level are used at amounts of at least 200 ppm, more specifically from 200 ppm to 10,000 ppm, based upon the sum of the weight of the 1,1,1,2,3,3,3-heptamethyl-trisiloxane and the ethenyl-oxa-bicyclo[4.1.0]heptane.

Other promoters include hindered amines, hindered phosphines, ketone-containing compounds, hydroxyl-containing compounds, and hydroxyl-substituted organic compounds. Representative and non-limiting examples of promoters include salts of carboxylic acid, such as sodium acetate, sodium propanoate, sodium octanoate, tetramethyl ammonium propanoate; hindered amine promoters, such as 2,2,6,6-tetramethyl-4-piperidinol, 2,2,6,6-tetramethylpiperidine, 1,2,2,6,6-pentamethyl-4-piperidinol, 1,2,2,6,6-pentamethylpiperidine, benzyldiisopropylamine, di-t-butylamine, dicyclohexylamine, N,N,N',N'-tetraisopropylethylenediamine, N -isopropylpiperidine, 2,2,6,6-tetramethyl-4(2-hydroxyethoxy)-, piperidine, and 2,2,6,6-tetramethyl-4-piperidone, and hindered phosphine promoters, such as tri-tert-butylphosphine, benzyldiisopropylphosphine, ethyl di-tert-butylphosphine, and di-tert-butylpentylphosphine.

The hydrosilylation reaction of 1,1,1,2,3,3,3-heptamethyl-trisiloxane with the ethenyl-oxa-bicyclo[4.1.0]heptane can be carried out with or without solvents. Typical solvents include hydrocarbons, such as toluene, xylenes, hexanes, heptanes, cyclohexanes, and the like and ethers such as tetrahydrofuran, diethyl ether, dimethoxyethane, and the like.

The reaction product of the hydrosilylation reaction, [bis-(trimethylsiloxy)methylsilanyl-ethyl]-7-oxabicyclo[4.1.0] heptane can be further purified to remove impurities, byproducts and unreacted starting materials. It is understood that the starting ethenyl-7-oxa-bicyclo[4.1.0]heptane is a mixture of isomers after epoxidation, unless the stereoisomers are separated, as by for example, distillation. The epoxidation of 4-vinylcyclohexene produces a mixture of from 40 to 60 weight percent cis-3-ethenyl-7-oxa-bicyclo [4.1.0]heptane and 40 to 60 weight percent trans-3-ethenyl-7-oxa-bicyclo[4.1.0]heptane, based upon the total weight of the two stereoisomers. It is preferable to separate the stereoisomers prior to the hydrosilylation reaction because the boiling points of the reactant ethenyl-7-oxa-bicyclo[4.1.0] heptane is lower, thereby facilitating the purification and separation process. Alternatively, the stereoisomers of [bis-(trimethylsiloxy)methylsilanyl-ethyl]-7-oxabicyclo[4.1.0] heptane can be separated to produce the stereoisomer which promotes addition of the (meth)acrylate to the desired position on the cyclohexyl ring.

The ring-opening reaction of the [bis-(trimethylsiloxy) methylsilanyl-ethyl]-7-oxabicyclo[4.1.0]heptane can occur in the presence or absence of a catalysts. It is preferred to carry out the reaction in the presence of catalysts which prevent the beta-hydroxyl group that is formed in the addition reaction from further reacting with the oxirane ring of the [bis-(trimethylsiloxy)methylsilanyl-ethyl]-7-oxabicyclo[4.1.0]heptane, thereby forming dimers or oligomers of the (meth)acryloxy containing trisiloxane. Catalysts for the reaction can be Bronsted acids or bases, Lewis acid or bases. Specifically, alkali metal hydroxides or alkaline earth metal hydroxides, mineral acids, metal salts or metal chelates can be used. In particular, metal salts or chelates of titanium, zinc, tin, bismuth, zirconium, and the like can be used. Preferably, titanium tetraalkoxides are used, where the alkoxy group are derived from a monoalcohol containing from 1 to 12 carbon atoms. Representative and non-limiting examples of titanium tetraalkoxides include titanium tetramethoxide, titanium tetraethoxide and titanium tetraisoproproxide.

The reaction of the [bis-(trimethylsiloxy)methylsilanyl-ethyl]-7-oxabicyclo[4.1.0]heptane with the methacrylic acid or acrylic acid or their salts occur at a temperature of from 15° C. to 180° C., at subatmospheric, atmospheric or superatmospheric pressure. Preferably, the reaction is carried out at a temperature of from 60° C. to 120° C. at atmospheric pressure.

In order to prevent polymerization of the activated carbon-carbon double bond of the acryloxy or methacryloxy group, the reaction is carried out in the presence of a polymerization inhibitor. The polymerization inhibitors include phenols, hydroquinone, aromatic amines and derivatives of piperidine-N-oxyl radicals. Representative and non-limiting examples of polymerization inhibitors include hydroquinone, hydroquinone monomethyl ether, 2,6-di-tert-butyl-4-methyl phenol, 4-hydroxy-2,2,6,6-tetramethylpiperidine-N-oxyl radical, 2,2,6,6-tetramethylpiperidine-N-oxyl radical, and the like.

Silicone hydrogel films obtained from trisiloxane monomers containing a 3-(meth)acryloxy-substituted (hydroxylcyclohexyl)ethyl group show high oxygen permeability due to the 1,3-substitution of the (meth)acryloxy and 2-bis-(trimethylsiloxy)methylsilanyl-ethyl groups on a cyclohexyl linking group. Although not to be held to any theory, the trans-1,3-substitution of the cyclohexyl group is believed to introduce more randomness (entropy) into the polymer containing the monomer of the present invention, thereby introducing a large free volume and better oxygen permeability. The hydroxyl functional groups of the compounds of the present invention, along with the hydrophilic monomers allow the silicone hydrogel films to have sufficient amounts of water and small enough regions of silicone containing units to provide for films that do not cause eye irritation, redness and other corneal complications which may result from direct contact of the eye with regions of high silicone content and hence restrict use of the lenses to limited periods of wear.

The trisiloxanes containing a 3-(meth)acryloxy-substituted (hydroxylcyclohexyl)ethyl group of the present invention can be used to obtain cured elastomers with desirable physical strength and resistance to tearing after absorption of water. The use of trisiloxane containing a 3-(meth)acryloxy-substituted (hydroxylcyclohexyl)ethyl group of the present invention in biomedical devices, especially in contact lenses, is further described in the sections below.

The present invention also provides silicone-hydrogel compositions comprising trisiloxanes containing a 3-(meth)acryloxy-substituted (hydroxycyclohexyl)ethyl group and at least one conventional organic monomer (also called co-monomer). The novel copolymers comprise one or more of the trisiloxanes containing a 3-(meth)acryloxy-substituted (hydroxycyclohexyl)ethyl group copolymerized with one or more of an alkyl 2-alkenoate, cycloalkyl 2-alkenoate, vinyl-containing aryl compound, vinyl-containing aralkyl compound and a relatively small amount of a cross-linking monomer. In general, novel copolymers containing from 20 to 80 parts by weight of the trisiloxane containing a 3-(meth)acryloxy-substituted (hydroxylcyclohexyl)ethyl group and from 80 to 20 parts of the 2-alkenoate, vinyl-containing aryl, vinyl-containing aralkyl monomer having a wide spectrum of suitable properties can be prepared. In one embodiment of the invention, the novel copolymers contain 30 to 55 parts by weight of the trisiloxane containing a 3-(meth)acryloxy-substituted (hydroxylcyclohexyl)ethyl group copolymerized with 70 to 45 parts by weight of a $C_1$-$C_4$ alkyl methacrylate and/or acrylate, and/or a cyclohexyl methacrylate and/or acrylate, preferably with a small amount of a cross-linking monomer.

Representative and non-limiting comonomers include methyl methacrylate, ethyl methacrylate, butyl methacrylate, 2-ethylhexyl acrylate, cyclohexyl methacrylate, methyl acrylate, 2-hydroxyethyl methacrylate (HEMA), N-vinylpyrrolidone (NVP), methacrylic acid (MA), and dimethylacrylamide (DMA), styrene, alpha-methylstyrene and mixtures thereof.

The cross-linking agent may be present in an amount of up to 5 weight percent and higher, desirably from 0.1 to 3 weight percent, and preferably up to 2 weight percent, based on the total monomers. The cross-linking agent, including mixtures thereof, can be any of the conventional ethylenically unsaturated compounds containing at least two polymerizable ethylenic bonds. Thus, there can be used alkylene glycol and polyalkylene glycol esters of acrylic acid, methacrylic acid, or crotonic acid and divinylbenzene.

Representative and non-limiting examples of crosslinkers include ethylene glycol diacrylate, ethylene glycol dimethacrylate, propylene glycol diacrylate, propylene glycol dimethacrylate, 1,4-butylene glycol dimethacrylate, ethylene glycol dicrotonate, diethylene glycol dimethacrylate, diethylene glycol diacrylate, dipropylene glycol dimethacrylate, dipropylene glycol diacrylate, trimethylene glycol diacrylate, triethylene glycol dimethacrylate, triethylene glycol dicrotonate, tetraethylene glycol dimethacrylate, hexaethylene glycol dimethacrylate, tripropylene glycol diacrylate, tripropylene glycol dimethacrylate, tetrapropylene glycol dimethacrylate, tributylene glycol dimethacrylate, tetrabutylene glycol dimethacrylate, hexamethylene glycol dimethacrylate, octamethylene glycol dimethacrylate, and decamethylene glycol dimethacrylate. Other suitable cross-linking agents include allyl methacrylate, divinylbenzene, diallyl phthalate, trimethylolpropane trimethacrylate, diallyl tartrate, diallyl maleate, triallylmelamine, N,N'-methylenebisacrylamide, divinyl citraconate, diallyl fumarate, divinyl sulfone, triallyl phosphite, diallyl benzenephosphonate, hexahydro-1,3,5-triacryltriazine, divinyl ether, and triallyl citrate. Also useful as cross-linking agents are the polysiloxanyl-containing polyethylenically unsaturated compounds such as polysiloxanylbis(alkylglycerol acrylate) and polysiloxanylbis(alkylglycerol methacrylate).

The trisiloxanes containing a 3-(meth)acryloxy-substituted (hydroxycyclohexyl)ethyl group of the present invention are miscible with hydrophilic co-monomers without the need for any homogenizing solvent, thereby affording silicone hydrogels that are transparent across the entire range of monomer-co-monomer compositions.

The high oxygen permeability of the novel copolymers is mainly due to its siloxane content. However, the greater the number of siloxane bonds in the novel copolymer, the greater the tendency of an undesirable water-repellent characteristic developing in the polymer. In such an eventuality it may be desirable to include in the polymerization mixture hydrophilic monomer such as the 2-hydroethyl methacrylate, 2-hydroethyl acrylate, N-vinylpyrrolidone, N,N-dimethylacrylamide along with other co-monomers.

Polymerization can be carried out under conventional conditions. Thus, for example, polymerization can be carried out specifically at 20° C. to 80° C. and more specifically at 25° to 45° C. The polymerization can be carried out employing a catalytically significant quantity of a free radical catalyst ranging in concentration from 0.05 to 1 percent based on the total weight of polymerizable monomers. Representative and non-limiting free radical catalysts include t-butyl peroctoate, benzoyl peroxide, isopropyl percarbonate, 2,4-dichlorobenzoyl peroxide, methyl ethyl ketone peroxide, cumene hydroperoxide, and dicumyl peroxide. Additional free radical polymerization initiators which can be used include bis-(tert-butylcyclohexyl)-peroxydicarbonate, azobisisobutyronitrile, and azobisdimethylvaleronitrile. Irradiation by ultraviolet light, gamma rays, and high energy radiation, such as with cobalt 60 radiation can be used to polymerize the monomers.

The copolymers of the present invention are clear (no haze from poor miscibility) polymers that absorb 10 weight percent to 60 weight percent of water, showing excellent surface wettability and effective oxygen permeability, all of which are necessary for the better comfort when lens are worn and for good health of the human cornea. The present invention also provides contact lenses made from the silicone-hydrogel films of the claimed invention. The contact lenses produced from the silicone-hydrogel films of the present invention do not require any expensive secondary treatments, like plasma oxidation or plasma coating, or internal wetting agents to improve wettability. That is, the contact lenses produced from silicone-hydrogel films of the present invention, without secondary treatment, are soft, flexible and inherently wettable and exhibit high oxygen permeability.

The present invention is also directed to copolymers formed by the reaction trisiloxane containing a 3-(meth) acryloxy-substituted (hydroxylcyclohexyl)ethyl group with other activated carbon-carbon double bond containing monomers and crosslinkers. These copolymers are made from one or more trisiloxane containing a 3-(meth)acryloxy-substituted (hydroxylcyclohexyl)ethyl group of the present invention and at least one other hydrophilic unsaturated organic monomer suitable for use in silicone hydrogels. These hydrophilic unsaturated organic monomers include the representative and non-limiting examples N,N-dimethylacrylamide, 2-hydroxy-ethyl-methacrylate (HEMA), N-vinylpyrrolidone, and methacrylic acid. In such copolymers, the copolymer ratio of the trisiloxane containing a 3-(meth) acryloxy-substituted (hydroxylcyclohexyl)ethyl group of the present invention to the other activated carbon-carbon double bond containing monomers is from 1:100 to 100:1, preferably from 1:20 to 20:1 and more preferably from 1:2 to 2:1.

In one particular embodiment, a copolymer is prepared from 40 to 60 weight percent of trisiloxane containing 3-(meth)acryloxy-substituted (hydroxylcyclohexyl)ethyl group of the present invention, 20 to 30 weight percent of dimethylacrylamide, 15 to 25 weight percent 2-hydroxyethyl (meth)acrylate, 1 to 10 weight percent N-vinyl pyroline and 0.1 to 3 weight percent of ethylene glycol dimethyl acrylate, based on the total weight of trisiloxane containing 3-(meth)acryloxy-substituted (hydroxylcyclohexyl)ethyl group of the present invention, dimethylacrylamide, 2-hydroxyethyl (meth)acrylate, N-vinyl pyroline and ethylene glycol dimethyl acrylate.

To form copolymers using the monomers of the present invention, the desired monomers are mixed and the resulting mixture is polymerized and cured to form transparent thin films by known thermal or UV cure techniques, using either peroxides or photoinitiators in the presence of crosslinking agents. The monomers added to the monomer mix to create the mixture prior to polymerization to form the copolymers may be monomers or prepolymers. A "prepolymer" is a reaction intermediate polymer of medium molecular weight having polymerizable groups.

The copolymers of the present invention form a clear, transparent homogeneous single-phase solution that can be cured directly without employing any additional homogenizing solvents. The trisiloxane containing a 3-(meth)acryloxy-substituted (hydroxylcyclohexyl)ethyl group of the present invention are miscible with hydrophilic hydrogel monomers. Calculated solubility parameter values based on Fedors method (Robert F. Fedors, Polymer Engineering and Science, February 1974, vol. 14, No. 2) for the present inventive monomers range from approximately 16.5 to approximately 19 $(J/mol)^{1/2}$, which is closer to the solubility parameter value of conventional hydrogel monomers (such as HEMA, NVP and DMA) than silicone monomers such as TRIS. Miscibility is realized if the difference in solubility parameter between the instant inventive monomers and the hydrophilic co-monomers is less than about 7.3 $(J/mol)^{1/2}$.

In another embodiment of the present invention, the polymers may be formed into silicone-hydrogel films, by processes known in the art. The silicone-hydrogel films of the present invention are soft, flexible and highly transparent. The present silicone hydrogel films were found to have dynamic advancing contact angles with water, in the range of 80° to 30° and absorb about 10 to 60 wt. % of water, which can vary depending the other hydrophilic unsaturated organic monomer used in preparing the silicone-hydrogel films. The silicone hydrogels produced were also found to have good mechanical properties (such as low modulus and high tear strength) required for the contact lens application.

Conventional silicone-hydrogel films are generally produced by curing a mixture of hydrophobic silicone monomers and hydrophilic hydrogel monomers in the presence of about 10 to 40 wt. % of solvent, as they are incompatible with each other. However in the current invention, the trisiloxane containing a 3-(meth)acryloxy-substituted (hydroxycyclohexyl)ethyl group are found to be miscible with conventional hydrophilic hydrogel monomers (such as HEMA, NVP and DMA) and can form a homogeneous solution suitable to produce silicone-hydrogel films without employing any solvent.

In the present invention, the resulting polymers may be formed into silicone-hydrogel films, via processes known in the art. Accordingly, the present invention is also directed to contact lens produced from either homo or copolymers of the present invention. The monomers/polymers of the present invention can be formed into contact lenses by spincasting processes, as disclosed in U.S. Pat. Nos. 3,408,429 and 3,496,254, cast molding processes, as disclosed in U.S. Pat. Nos. 4,084,459 and 4,197,266, combinations of methods thereof, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

The relative softness or hardness of the contact lenses fabricated from the resulting polymer of this invention can be varied. Generally, as the ratio of trisiloxane containing a 3-(meth)acryloxy-substituted (hydroxylcyclohexyl)ethyl group increases relative to the other monomers used in preparing the polymer, the softness of the material increases.

The copolymers of this invention may also contain ultraviolet absorbents, pigments and colorants in the form of additives or co-monomers.

The silicone-hydrogels of the present invention exhibit high oxygen transport with surface wettable properties. The monomers and prepolymers employed in accordance with this invention are readily polymerized to form three-dimensional networks, which permit the transport of oxygen with improved wettability along with desirable mechanicals and optical clarity.

Specific use of the films include intraocular contact lenses, artificial corneas, and soft disposable long-wear contact lenses or as coatings for biomedical devices.

In another embodiment of the present invention, other specific used of trisiloxanes containing a 3-(meth)acryloxy-substituted (hydroxylcyclohexyl)ethyl group and copolymers made therefrom are as additives or resin for coatings and adhesives. Coatings containing the additive or copolymer of the present invention may show a number of superior properties, including lower surface energy, slip, soft feel, flow and leveling, water resistance and release properties. These properties are of particular interest in coatings for graphic, textile, plastic, wood, architectural, automotive, metal and pressure sensitive adhesive applications. The monofunctionality of the trisiloxane monomer containing a 3-(meth)acryloxy-substituted (hydroxylcyclohexyl)ethyl group prevents excessive viscosity buildup during polymer synthesis. The coatings containing the novel trisiloxanes containing a 3-(meth)acryloxy-substituted (hydroxylcyclohexyl)ethyl group (additive) and copolymers made thereform of the present invention may include powder coatings, conversion coatings, passivation coatings, primers, high solids coating, waterborne coatings, solventborne coatings, e-coatings, hardcoats and the like.

The following Examples are illustrative only and should not be construed as limiting the invention. All parts and percentages are by weight and all temperatures are in degrees Celsius unless explicitly stated otherwise.

EXAMPLES

The silicone-hydrogel films produced were evaluated for lens properties using the following methods.

Equilibrium Water Content.

The film was immersed in deionized water for 48 hours. Then the surface water was wiped off gently using lintless tissue paper. The hydrated film was weighed precisely and then dried in an oven at 37° C. for 48 hours and weighed again for dry weight. Water content was calculated based on weight change using the following equation.

$$\% \text{ Water content} = \frac{[\text{Weight of hydrated lens} - \text{Weight of dry lens}] \times 100\%}{\text{Weight of hydrated lens}}$$

Water Wettability.

Water wettability was measured according to: Neumann A W, Godd R J. Techniques of measuring contact angles. In: Good R J, Stromberg R R, Editors. Surface and Colloid science—Experimental methods, vol. 11. New York: Plenum Publishing; (1979), pp. 31-61.

Water wettability of the film surface was evaluated by measuring contact angle using both a dynamic contact angle method and a captive air bubble method with a Rame Hart NRL CA. goniometer. In the dynamic contact angle method the wet films were first pressed with lintless tissue paper and then a drop of water was placed on the surface. The contact angle was measured with respect to time using a goniometer. In the captive bubble method, which better simulates the on eye conditions, an air bubble injected from a syringe is brought into contact with the film immersed in Milli-Q water and the contact angle is then measured. Lower contact angle values represent a greater degree of hydrophilicity or better surface wettability of the film.

Oxygen Permeability (Dk Value).

The oxygen permeability (Dk) for these samples was measured using polarographic technique following ISO 9913 standards method. The film was clamped into the permeation cell and the donor chamber was filled with oxygen saturated PBS (phosphate buffered saline). The concentration of oxygen in the receptor cell was monitored, and plotted as a function of time and the permeability was determined from the initial slope of the plot.

Oxygen permeability, also called the Dk value, which may be expressed in Barrer, wherein 1 Barrer=$10^{-11}$ ($cm^3$ $O_2$) cm $cm^{-2}s^{-1}$ $mmHg^{-1}$, wherein ($cm^3$ $O_2$) is at a quantity of oxygen at standard temperature and pressure and wherein cm represents the thickness of the material and $cm^{-2}$ is the reciprocal of the surface area of that material or $3.348\times10^{-19}$ kmol m/($m^2$ s Pa). The Dk of water is 80 Barrer.

Modulus.

The Young's modulus of the hydrated film was measured using an Instron tensile tester. The wet samples were cut into 6 cm×0.8 cm strips and the mechanical properties were measured with a load cell of 50 N and crosshead speed of 10 mm/minute. The modulus was determined from the initial slope of a stress-strain curve. Modulus is directly correlated to the softness of the material. Lower the modulus, softer the material.

Refractive Index.

The refractive index was measured in accordance with ASTM D1218, Standard Test Method for Refractive Index and Refractive Dispersions of Hydrocarbon Liquids, at 20° C.

Density.

The density was measured in accordance with ASTM D891-09, Method for Specific Gravity, Apparent, of Liquid Industrial Chemicals, at 20° C.

Example 1

Preparation of Acrylic Acid trans-2-hydroxy-trans-5-[2-bis-(trimethylsiloxy)methylsilanyl-ethyl]-cyclohexyl ester Using a Titanium Alkoxide Catalyst for the Epoxy Ring Opening Reaction Into a 500 mL round bottom flask equipped with a temperature controller, heating mantel, and condenser 3-ethenyl-7-oxabicyclo[4.1.0]heptane (57.8 grams, 0.47 mole) was added. The solution was stirred with a magnetic stirrer and heated to 75° C. Chloroplatinic acid (20 ppm) was added followed by the slow addition of 1,1,1,3,5,5,5-heptmethyltrisiloxane (100 g, 0.45 mol) via an addition funnel. The exotherm was not allowed to go above 85° C. After the addition the reaction was held at 75° C. for 2 hours. The resulting product was distilled through a 6 inch Vigreux column under a 0.9 torr vacuum. The product, 3-[bis-(trimethylsiloxy)methylsilanyl-ethyl]-7-oxabicyclo[4.1.0] heptane, evolved between 110 and 120° C. The pure product (151.1 grams, 96% yield) was a clear colorless fluid.

3-[Bis-(trimethylsiloxy)methylsilanyl-ethyl]-7-oxabicyclo[4.1.0]heptane (100 grams, 0.288 moles), 2,2,6,6-tetramethylpiperidine-N-oxyl (0.0034 gram), and titanium tetraethoxide (0.44 grams) was charged into a 3-necked round bottom flask equipped with a magnetic stirrer. The flask was heated to 90° C. Acrylic acid (20.8 grams, 0.288 moles) was then added to the flask and stirred at 90° C. and atmospheric pressure over a period of 8 hours. The reaction flask was then heated at 90° C. for an additional 3 hours. The product was cooled to room temperature and stored under nitrogen. The analyses of the product by gas chromatography and gas-chromatography/mass spectrometry revealed:

| | |
|---|---|
| 0.4 weight % | 3-[bis-(trimethylsiloxy)methylsilanyl-ethyl]-7-oxabicyclo[4.1.0]heptane |
| 42.0 weight % | acrylic acid trans-2-hydroxy-trans-5-[2-bis-(trimethylsiloxy)methylsilanyl-ethyl]-cyclohexyl ester |
| 4.5 weight % | acrylic acid cis-2-hydroxy-trans-5-[2-bis-(trimethylsiloxy)methylsilanyl-ethyl]-cyclohexyl ester |
| 43.4 weight % | acrylic acid trans-2-hydroxy-trans-4-[2-bis-(trimethylsiloxy)methylsilanyl-ethyl]-cyclohexyl ester |

| | |
|---|---|
| 2.9 weight % | acrylic acid cis-2-hydroxy-trans-4-[2-bis-(trimethylsiloxy)methylsilanyl-ethyl]-cyclohexyl ester |
| 0.8 weight % | acrylic acid 2-acryloyloxy-5-[bis-(trimethylsiloxy)methylsilanyl-ethyl]-cyclohexyl ester |
| 3.3 weight % | acrylic acid 5-[bis-(trimethylsiloxy)methylsilanyl-ethyl]-2-(5-[bis-(trimethylsiloxy)methylsilanyl-ethyl]-2-hydroxy-cyclohexyloxy)-cyclohexyl ester and related dimers. |

The use of the titanium tetraethoxide catalyst for the epoxy ring opening reaction produced a reaction product that had very low levels of dimer or oligomeric components.

Example 2

Preparation of Acrylic Acid trans-2-hydroxy-trans-5-[2-bis-(trimethylsiloxy)methylsilanyl-ethyl]-cyclohexyl ester in the Absence of a Epoxy Ring Opening Catalyst Into a 500 mL round bottom flask equipped with a temperature controller, heating mantel, and condenser 3-ethenyl-7-oxabicyclo[4.1.0]heptane (57.8 grams, 0.47 mole) was added. The solution was stirred with a magnetic stirrer and heated to 75° C. Chloroplatinic acid (20 ppm) was added followed by the slow addition of 1,1,1,3,5,5,5-heptamethyltrisiloxane (100 g, 0.45 mol) via an addition funnel. The exotherm was not allowed to go above 85° C. After the addition the reaction was held at 75° C. for 2 hours. The resulting product was distilled through a 6 inch Vigreux column under a 0.9 torr vacuum. The product, 3-[bis-(trimethylsiloxy)methylsilanyl-ethyl]-7-oxabicyclo[4.1.0]heptane, evolved between 110 and 120° C. The pure product (151.1 grams, 96% yield) was a clear colorless fluid.

3-[Bis-(trimethylsiloxy)methylsilanyl-ethyl]-7-oxabicyclo[4.1.0]heptane (50 grams, 0.144 moles), and 2,2,6,6-tetramethylpiperidine-N-oxyl (0.0021 gram), were charged into a 3-necked round bottom flask equipped with a magnetic stirrer. The flask was heated to 90° C. Acrylic acid (10.4 grams, 0.144 mole) was then added to the flask using a syringe pump at a rate of 0.043 mL/minute over a period of 4 hours. The mixture in the reaction flask was heated at 90° C. for an additional 3 hours. The reaction product was cooled to room temperature and stored under nitrogen. The analyses of the product by gas chromatography and gas-chromatography/mass spectrometry revealed:

| | |
|---|---|
| 9.1 weight % | 3-[bis-(trimethylsiloxy)methylsilanyl-ethyl]-7-oxabicyclo[4.1.0]heptane |
| 27.1 weight % | acrylic acid trans-2-hydroxy-trans-5-[2-bis-(trimethylsiloxy)methylsilanyl-ethyl]-cyclohexyl ester |
| 2.3 weight % | acrylic acid cis-2-hydroxy-trans-5-[2-bis-(trimethylsiloxy)methylsilanyl-ethyl]-cyclohexyl ester |
| 26.2 weight % | acrylic acid trans-2-hydroxy-trans-4-[2-bis-(trimethylsiloxy)methylsilanyl-ethyl]-cyclohexyl ester |
| 1.4 weight % | acrylic acid cis-2-hydroxy-trans-4-[2-bis-(trimethylsiloxy)methylsilanyl-ethyl]-cyclohexyl ester |
| 0.3 weight % | acrylic acid 2-acryloyloxy-5-[bis-(trimethylsiloxy)methylsilanyl-ethyl]-cyclohexyl ester |
| 31.8 weight % | acrylic acid 5-[bis-(trimethylsiloxy)methylsilanyl-ethyl]-2-(5-[bis-(trimethylsiloxy)methylsilanyl-ethyl]-2-hydroxy-cyclohexyloxy)-cyclohexyl ester and related dimers. |

When the reaction between the 3-[bis-(trimethylsiloxy)methylsilanyl-ethyl]-7-oxabicyclo[4.1.0]heptane and acrylic acid is carried out in the absence of the titanium tetraethoxide epoxy ring opening reaction, the product contained significant amounts of the acrylic acid 5-[bis-(trimethylsiloxy)methylsilanyl-ethyl]-2-(5-[bis -(trimethylsiloxy)methylsilanyl-ethyl]-2-hydroxy-cyclohexyloxy)-cyclohexyl ester, and related dimers.

Example 3

Preparation of acrylic acid trans-2-hydroxy-trans-5-[2-bis-(trimethylsiloxy)methylsilanyl-ethyl]-cyclohexyl ester using cis-3-ethenyl-7-oxabicyclo[4.1.0]heptane Into a 5 L round bottom flask equipped with a temperature controller, heating mantel, 160 cm rectification column packed with metal shavings and condenser, a mixture of cis and trans-3-ethenyl-7-oxabicyclo[4.1.0]heptane (2,000 grams) is distilled at atmospheric pressure to obtain cis-3-ethenyl-7-oxabicyclo[4.1.0]heptane.

Into a 500 mL round bottom flask equipped with a temperature controller, heating mantel, and condenser cis-3-ethenyl-7-oxabicyclo[4.1.0]heptane (57.8 grams, 0.47 mole) is added. The solution is stirred with a magnetic stirrer and is heated to 75° C. Chloroplatinic acid (20 ppm) is added followed by the slow addition of 1,1,1,3,5,5,5-heptamethyltrisiloxane (100 g, 0.45 mol) via an addition funnel. The exotherm is not allowed to go above 85° C. After the addition, the reaction is held at 75° C. for 2 hours. The resulting product is distilled through a 6" Vigreux column under a 0.9 torr vacuum. The product, cis-3-[bis-(trimethylsiloxy)methylsilanyl-ethyl]-7-oxabicyclo[4.1.0]heptane, is obtained.

Cis-3-[bis-(trimethylsiloxy)methylsilanyl-ethyl]-7-oxabicyclo[4.1.0]heptane (100 grams, 0.288 moles), 4-hydroxy-2,2,6,6-tetramethylpiperidine-N-oxyl (0.0034 gram), and titanium tetraethoxide (0.44 grams) are charged into a 3-necked round bottom flask equipped with a magnetic stirrer. The flask is heated to 90° C. Acrylic acid (20.8 grams, 0.288 moles) is added slowly to the flask via an addition funnel and the reaction mixture is stirred at 90° C. and atmospheric pressure over a period of 8 hours. The reaction flask is heated at 90° C. for an additional 3 hours. The product is cooled to room temperature and stored under nitrogen.

When only the cis-isomer of cis-3-ethenyl-7-oxabicyclo[4.1.0]heptane is used in the preparation of the acrylic acid trans-2-hydroxy-trans-5-[2-bis -(trimethylsiloxy)methylsilanyl-ethyl]-cyclohexyl ester, the product may be enriched in the desired stereoisomer.

Comparative Example A

Preparation of 2-methyl-acrylic acid 2-[2-(3-trimethylsilanyl-propoxy)-hepta-ethoxy]-ethyl ester 1,1,1,3,5,5,5-Heptamethyl-trisiloxane (70 gram, 0.32 mole) and a methallyl-terminated polyethylene glycol, having an average of eight ethylene oxide (EO) units in the chain (125 grams, 0.30 mole) were introduced into a 500 mL three-neck round bottom flask equipped with a reflux condenser, mechanical stirrer, temperature controller with thermocouple and a nitrogen inlet. The contents were heated to 80° C.-85° C. in the presence of Karstedt's catalyst (platinum complex of 1,3-divinyltetramethyldisiloxane, 30 ppm Pt based on weight of total reactants charged) and 50 ppm sodium propionate buffer to prevent side reactions like dehydrocoupling reaction from taking place. After completion of the hydrosilylation, volatile compounds were distilled (stripped) under reduced pressure. The product, hydroxyl-terminated silicone polyether, was obtained as a colorless, transparent liquid in quantitative yield without any undesired side products.

The hydroxyl-terminated silicone polyether (201 grams, 0.32 mole) that was synthesized in the step above, triethylamine (30.3 grams) and methyl ethyl ketone (250 ml) were introduced into a three-neck one liter round bottomed flask equipped with dropping funnel and a stirring blade. The flask was immersed in an ice bath and methacryloyl chloride (31.2 grams, 0.30 mole) was added drop wise over a period of approximately 1 hour with constant stirring. After completion of the addition, the stirring was continued for another 3 hours at room temperature. The triethylamine hydrochloride salt thus formed precipitated out during the reaction. The solvent was removed with a rotary vacuum evaporator and the final monomer was obtained as a colorless, transparent liquid. The low boiling point of the solvent used enabled the solvent to be removed completely at a temperature of about 30° C. to 40° C. under vacuum of 10 mm Hg. The resulting hydrophilic monomer product was colorless to pale yellow.

Example 4

Density, Refractive Index and Solubility Parameters for Co-Monomers and Reaction Product of Example 1 Used in Making Silicone-Hydrogels The density and refractive index are measured for a series of monomers used in making hydrogels by ASTM methods D1218 and D891-09 at 20° C. The solubility parameters were calculated using the method based on Fedors method (Robert F. Fedors, Polymer Engineering and Science, February 1974, vol. 14, No. 2). The results are reported in Table I.

TABLE I

Density, refractive index, and solubility parameters for monomers used in making hydrogels and product of Example 1.

| Compound | Refractive Index | Density (g/mL) | Solubility Parameter $(J/mol)^{1/2}$ |
|---|---|---|---|
| Example 1 | 1.453 | 0.978 | 18.7 |
| TRIS[1] | 1.419 | 0.918 | 16.0 |
| Comp. Example A[2] | 1.448 | 1.012 | 17.3 |
| HEMA[3] | 1.454 | 1.079 | 24.6 |
| DMA[5] | 1.473 | 0.962 | 21.6 |
| NPV[5] | 1.512 | 1.04 | 25.3 |

[1]TRIS is 3-methacryloxypropyl-tris-(trimethylsiloxy)silane.
[2]Comp. Example A is 2-methyl-acrylic acid 2-[2-(3-trimethylsilanyl-propoxy)-heptaethoxy]-ethyl ester.
[3]HEMA is 2-hydroxyethyl methacrylate.
[4]DMA is dimethylacrylamide
[5]NPV is N-vinyl pyrollidone.

The differences in solubility parameter between the 3-acryloxy-substituted (hydroxycyclohexyl)ethyl trisiloxane of Example 1 and the organic hydrophilic co-monomers in the table are in the range 2.9-6.6 $(J/mol)^{1/2}$ and are all less than the 7.3 $(J/mol)^{1/2}$ criterion cited hereinabove. These data indicate that the (meth)acryloxy-containing trisiloxane having a 3-(meth)acryloxy-substituted (hydroxylcyclohexyl)ethyl group of the present invention can be polymerized with hydrophilic monomers without the need of a co-solvent to improve miscibility of the reactants.

Example 5

Preparation of Silicone-Hydrogel Using Compound of Example 1 and 2-hydroxyethyl methacrylate co-monomer The compound obtained in Example 1 (49 parts by weight), 2-hydroxyethyl methacrylate (49 parts by weight), ethylene glycol dimethacrylate (EGDMA, 0.5 part by weight), and benzoyl peroxide (0.5 parts by weight) were mixed and stirred. The resulting clear, homogeneous and transparent reaction mixture was purged with nitrogen gas and poured into a steel mold and cured at 85° C. to 90° C. for 5 to 6 hours in a hot air oven. The film thickness was between 1 to 2 millimeters. After curing, the film was released from the mold by submerging it in boiling water. The leachable monomers were removed using isopropanol-water wash. The film was then stored in deionized water.

The silicone hydrogel film produced was transparent, soft and flexible and had the properties reported in Table II.

Comparative Example B

Preparation of Silicone-Hydrogel Using Compound of Comparative Example A

The compound obtained in Comparative Example A (49 parts by weight), 2-hydroxy ethylmethacrylate (49 parts by weight), ethylene glycol dimethacrylate (EGDMA, 0.5 part by weight), and benzoyl peroxide (0.5 parts by weight) were mixed and stirred. The resulting clear, homogeneous and transparent reaction mixture was purged with nitrogen gas and poured into a steel mold and cured at 85° C. to 90° C. for 5 to 6 hours in a hot air oven. The film thickness was between 1 to 2 millimeters. After curing, the film was released from the mold by submerging it in boiling water. The leachable monomers were removed using isopropanol-water wash. The film was then stored in deionized water.

The silicone hydrogel film produced was transparent and had the properties reported in Table II.

Comparative Example C

Preparation of Silicone-Hydrogel Using 3-methacryloxypropyl-tris-(trimethylsiloxy)silane and hydroxyethyl methacrylate Co-Monomer 3-Methacryoxypropyl tris-(trimethysiloxy)silane (49 parts by weight), 2-hydroxyethyl methacrylate (49 parts by weight), ethylene glycol dimethacrylate (EGDMA, 0.5 part by weight), and benzoyl peroxide (0.5 parts by weight) were mixed and stirred. The resulting clear, homogeneous and transparent reaction mixture was purged with nitrogen gas and poured into a steel mold and cured at 85° C. to 90° C. for 5 to 6 hours in a hot air oven. The film thickness was between 1 to 2 millimeters. After curing, the film was released from the mold by submerging it in boiling water. The leachable monomers were removed using isopropanol-water wash. The film was then stored in deionized water.

The silicone hydrogel film produced was transparent and had the properties reported in Table II.

TABLE II

Physical properties of hydrogels made with silicone containing reactive carbon-carbon double bonds.

| Example | Weight Percent Siloxane Content | % Transmittance | Percent water content | Young's Modulus, MPa |
|---------|------|------|------|------|
| 5 | 26 | 88 | 15 | 6.8 ± 0.5 |
| B | 16 | 96 | 25 | — |
| C | 35 | 60 | 15 | — |

The hydrogel made with the monomer of Example 5, had a low siloxane content of 26%, which translates into better feel and less corneal complications while maintaining clarity, as measured by % transmittance of 88% and good water content. The hydrogel made with 3-methacryloxypropyl-tris-(trimethylsiloxy)silane, Comparative Example C, had a high siloxane content of 35%, poor transmittance of 60% and good water pickup.

Example 6

Preparation of Hydrogel Using Compound of Example 1 and dimethylacrylamide co-monomer The compound obtained in Example 1 (49 parts by weight), dimethylacrylamide (49 parts by weight), ethylene glycol dimethacrylate (EGDMA) (1 part by weight), and 1,2-octanedione, 1-[4-(phenylthio)phenyl]-, 2-(O-benzoyloxime) (1 part by weight Irgacure OXE01) were mixed and stirred. The resulting clear, homogeneous and transparent reaction mixture was purged with nitrogen gas and poured into an aluminium pan covered with a polystyrene Petri dish. The thin film of the reaction mixture was exposed to UV radiation in a chamber at 15 mW/cm$^2$ for 20 minutes. After curing, the film was immersed in isopropyl alcohol and then placed in deionized water for 48 hours. The silicone hydrogel film produced was transparent, soft and flexible and had the properties reported in Table III.

Comparative Example D

Preparation of Silicone-Hydrogel Using Compound of Example 1 and N-vinylpyrrolidone co-monomer The compound obtained in Example 1 (49 parts by weight), N-vinylpyrrolidone (49 parts by weight), ethylene glycol dimethacrylate (EGDMA, 0.5 part by weight), and benzoyl peroxide (0.5 parts by weight) were mixed and stirred. The resulting clear, homogeneous and transparent reaction mixture was purged with nitrogen gas and poured into a steel mold and cured at 85° C. to 90° C. for 5 to 6 hours in a hot air oven. The film thickness was between 1 to 2 millimeters. After curing, the film was released from the mold by submerging it in boiling water. The leachable monomers were removed using isopropanol-water wash. The film was then stored in deionized water.

The silicone hydrogel film produced was transparent, soft and flexible and had the properties reported in Table III.

Example 8

Preparation of Silicone-Hydrogel Using Compound of Example 1

The compound obtained in Example 1 (49 parts by weight), 2-hydroxyethyl methacrylate (14.7 parts by weight), dimethylacrylamide (34.3 parts by weight), ethylene glycol dimethacrylate (EGDMA, 0.5 part by weight), and benzoyl peroxide (0.5 parts by weight) were mixed and stirred. The resulting clear, homogeneous and transparent reaction mixture was purged with nitrogen gas and poured into a steel mold and cured at 85° C. to 90° C. for 5 to 6 hours in a hot air oven. The film thickness was between 1 to 2 millimeters. After curing, the film was released from the mold by submerging it in boiling water. The leachable monomers were removed using isopropanol-water wash. The film was then stored in deionized water.

The silicone hydrogel film produced was transparent, soft and flexible and had the properties reported in Table III.

TABLE III

Physical properties of hydrogels made with acryloxy-containing trisiloxane have a 3-acryloxy-substituted (hydroxycyclohexyl)ethyl group.

| Example | Weight Percent Siloxane Content | % Transmittance | Percent water content | Young's Modulus, MPa |
|---------|------|------|------|------|
| 6 | 26 | 93 | 34 | 0.41 ± 0.1 |
| D | 26 | opaque | 9 | — |
| 8 | 26 | 96 | 30 | 0.45 ± 0.05 |

These results indicate clear, transparent silicone-hydrogels with high water content can be formed from acryloxy-containing trisiloxanes having a 3-acryloxy-substituted (hydroxycyclohexyl)ethyl group and hydrophilic co-monomers having solubility parameters within 7.3 (J/mol)$^{1/2}$ of the value of the trisiloxane In Example 8, a terpolymer of the compound of Example 1, 2-hydroxyethyl methacrylate and dimethylacrylamide had a very high OA transmittance, low siloxane content and good water content.

Example 9

Preparation of Silicone-Hydrogel Using Compound of Example 1, dimethylacrylamide and 2-hydroxyethyl methacrylate co-monomers The compound obtained in Example 1 (49 parts by weight), dimethylacrylamide (34.3 parts by weight), 2-hydroxyethyl methacrylate (14.7 parts) ethylene glycol dimethacrylate (EGDMA, 0.5 part by weight), and benzoyl peroxide (0.5 parts by weight) were mixed and stirred. The resulting clear, homogeneous and transparent reaction mixture was purged with nitrogen gas and poured into a steel mold and cured at 85° C. to 90° C. for 5 to 6 hours in a hot air oven. The film thickness was between 1 to 2 millimeters. After curing, the film was released from the mold by submerging it in boiling water. The leachable monomers were removed using isopropanol-water wash. The film was then stored in deionized water.

The silicone hydrogel film produced was transparent, soft and flexible and had the properties:

Percent water content: 30±2%

Captive bubble contact angle: 35±4 degrees

% Transmittance: greater than 95%

Modulus: 0.45±0.05 MPa

Example 10

Preparation of Hydrogel Using Compound of Example 1, dimethylacrylamide, 2-hydroxyethyl methacrylate, and N-vinyl pyrollidone co-monomers

The compound obtained in Example 1 (50 parts by weight), dimethylacrylamide (25 parts by weight), 2-hydroxyethylmethacrylate (20 parts), N-vinyl pyrollidone (5 parts by weight), ethylene glycol dimethacrylate (EGDMA, 0.5 part by weight), and benzoyl peroxide (0.5 parts by weight) were mixed and stirred. The resulting clear, homogeneous and transparent reaction mixture was purged with nitrogen gas and poured into a steel mold and cured at 85° C. to 90° C. for 5 to 6 hours in a hot air oven. The film thickness was between 1 to 2 millimeters. After curing, the film was released from the mold by submerging it in boiling water. The leachable monomers were removed using isopropanol-water wash. The film was then stored in deionized water. The silicone hydrogel film produced was transparent, soft and flexible and had the properties:

Percent water content: 25±2%
Captive bubble contact angle: 30±4 degrees
% Transmittance: greater than 95%
Modulus: 0.4±0.1 MPa While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:
1. A trisiloxane of the general Formula (I):

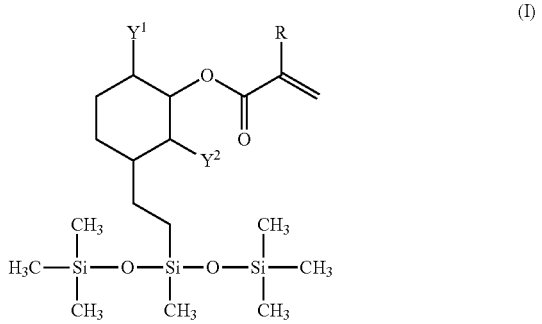

(I)

wherein R is hydrogen or methyl; $Y^1$ is hydrogen or hydroxyl; and, $Y^2$ is hydrogen or hydroxyl, with the proviso that at least one $Y^1$ or $Y^2$ is a hydroxyl group.

2. The trisiloxane of claim 1 selected from the group consisting of acrylic acid 2-hydroxy-5-[2-bis-(trimethylsiloxy)methylsilanyl-ethyl]-cyclohexyl ester, methacrylic acid 2-hydroxy-5-[2-bis-(trimethylsiloxy)methylsilanyl-ethyl]-cyclohexyl ester, acrylic acid 2-hydroxy-3-[2-bis-(trimethylsiloxy)methylsilanyl-ethyl]-cyclohexyl ester, methacrylic acid 2-hydroxy-3-[2-bis-(trimethylsiloxy)methylsilanyl-ethyl]-cyclohexyl ester, and mixtures thereof.

3. The trisiloxane of claim 2 wherein the trisiloxane is selected from the group consisting of acrylic acid trans-2-hydroxy-trans-5-[2-bis-(trimethylsiloxy)methylsilanyl-ethyl]-cyclohexyl ester, methacrylic acid trans-2-hydroxy-trans-5-[2-bis-(trimethylsiloxy)methylsilanyl-ethyl]-cyclohexyl ester, acrylic acid trans-2-hydroxy-trans-3-[2-bis-(trimethylsiloxy)-methylsilanyl-ethyl]-cyclohexyl ester, methacrylic acid trans-2-hydroxy-trans-3-[2-bis-(trimethylsiloxy)methylsilanyl-ethyl]-cyclohexyl ester, and mixtures thereof.

4. The trisiloxane of claim 1, wherein the trisiloxane has the stereochemical structure of Formula (II):

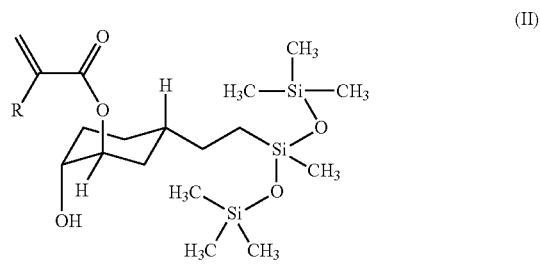

(II)

wherein R is hydrogen or methyl.

5. The trisiloxane of claim 3 comprising from 40 to 99 weight percent acrylic acid trans-2-hydroxy-trans-5-[2-bis-(trimethylsiloxy)methylsilanyl-ethyl]-cyclohexyl ester and from 1 to 60 weight percent of acrylic acid trans-2-hydroxy-cis-4-[2-bis-(trimethylsiloxy)methylsilanyl-ethyl]-cyclohexyl ester based on the total weight of the two isomers, or from 40 to 99 weight percent methacrylic acid trans-2-hydroxy-trans-5-[2-bis-(trimethylsiloxy)methylsilanyl-ethyl]-cyclohexyl ester and from 1 to 60 weight percent methacrylic acid trans-2-hydroxy-cis-4-[2-bis-(trimethylsiloxy)methylsilanyl-ethyl]-cyclohexyl ester based on the total weight of the two isomers.

6. A process for preparing trisiloxane of claim 1 which comprises:
   a) reacting ethenyl-oxa-bicyclo[4.1.0]heptane with 1,1,1,2,3,3,3-heptamethyl-trisiloxane in the presence of a hydrosilylation catalyst to provide a hydrosilylated product; and,
   b) reacting the hydrosilylated product of step (a) with (meth)acrylic acid, optionally in the presence of an oxirane ring-opening catalyst to produce trisiloxane of claim 1.

7. The process of claim 6 wherein greater than 85 weight percent of the ethenyl-oxa-bicyclo[4.1.0]heptane is 3-ethenyl-7-oxa-bicyclo[4.1.0]heptane which has the oxygen atom of the oxirane ring bonded to the 1 and 6-carbon atoms of the cyclohexyl ring in the C-1 equatorial and C-6 axial positions and has the ethenyl group bonded to the 3-carbon atom of the cyclohexyl ring in the equatorial position, or greater than 85 weight percent of the ethenyl-oxa-bidcyclo[4.1.0]heptane is 2-ethenyl-7-oxa-bicyclo[4.1.0]heptane which has the oxygen atom of the oxirane ring bonded to the 1 and 6-carbon atoms of the cyclohexyl ring in the C-1 axial and C-6 equatorial positions and has the ethenyl group bonded to the 2-carbon atom of the cyclohexyl ring in the equatorial position.

8. A copolymer obtained by the copolymerization of copolymerizable mixture comprising trisiloxane of claim 1, monomer containing an activated carbon-carbon double bond and crosslinker.

9. The copolymer of claim 8 wherein the monomer containing an activated carbon-carbon double bond is selected from the group consisting of methyl methacrylate, ethyl methacrylate, butyl methacrylate, 2-ethylhexyl acrylate, cyclohexyl methacrylate, methyl acrylate, 2-hydroxyethyl methacrylate, N-vinylpyrrolidone, methacrylic acid and dimethylacrylamide, and mixtures thereof.

10. The copolymer of claim 8 wherein the crosslinker is selected from the group consisting of ethylene glycol diacrylate, ethylene glycol dimethacrylate, propylene glycol diacrylate, propylene glycol dimethacrylate, 1,4-butylene glycol dimethacrylate, ethylene glycol dicrotonate, diethylene glycol dimethacrylate, diethylene glycol diacrylate, dipropylene glycol dimethacrylate, dipropylene glycol diacrylate, trimethylene glycol diacrylate, triethylene glycol diemthacrylate, triethylene glycol dicrotonate, tetraethylene glycol dimethacrylate, hexaethylene glycol dimethacrylate, tripropylene glycol diacrylate, tripropylene glycol dimethacrylate, tetrapropylene glycol dimethacrylate, tributylene glycol dimethacrylate, tetrabutylene glycol dimethacrylate, hexamethylene glycol dimethacrylate, octamethylene glycol dimethacrylate, decamethylene glycol dimethacrylate, allyl methacrylate, divinylbenzene, diallyl phthalate, trimethylolpropane trimethacrylate, diallyl tartrate, diallyl maleate, triallylmelamine, N,N'-methylenebisacrylamide, divinyl citraconate, diallyl fumarate, divinyl sulfone, triallyl phosphite, diallyl benzenephosphonate, hexahydro-1,3,5-triacryltriazine, divinyl ether, triallyl citrate, polysiloxanylbis(alkylglycerol acrylate), polysiloxanylbis(alkylglycerol methacrylate), and mixtures thereof.

11. The copolymer of claim 8 wherein the ratio of trisiloxane to monomer containing an activated carbon-carbon double bond is from 1:2 to 2:1.

12. The copolymer of claim 8 wherein the copolymerizable mixture comprises from 40 to 60 weight percent trisiloxane, from 20 to 30 weight percent dimethylacrylamide, from 15 to 25 weight percent 2-hydroxyethyl (meth)acrylate, from 1 to 10 weight percent N-vinylpyrrolidone and from 0.1 to 3 weight percent ethylene glycol dimethyl acrylate based on the total weight of the mixture.

13. A contact lens comprising copolymer of claim 8.

14. A contact lens comprising copolymer of claim 11.

15. A contact lens comprising copolymer of claim 12.

16. The contact lens of claim 13 wherein the trisiloxane is selected from the group consisting of acrylic acid 2-hydroxy-5-[2-bis-(trimethylsiloxy)methylsilanyl-ethyl]-cyclohexyl ester, methacrylic acid 2-hydroxy-5-[2-bis-(trimethylsiloxy)methylsilanyl-ethyl]-cyclohexyl ester, acrylic acid 2-hydroxy-3-[2-bis-(trimethylsiloxy)methylsilanyl-ethyl]cyclohexyl ester, methacrylic acid 2-hydroxy-3-[2-bis-(trimethylsiloxy)methylsilanyl-ethyl]-cyclohexyl ester, and mixtures thereof.

17. The contact lens of claim 13 wherein the trisiloxane is selected from the group consisting of acrylic acid trans-2-hydroxy-trans-5-[2-bis-(trimethylsiloxy)methylsilanyl-ethyl]-cyclohexyl ester, methacrylic acid trans-2-hydroxy-trans-5-[2-bis-(trimethylsiloxy)methylsilanyl-ethyl]-cyclohexyl ester, acrylic acid trans-2-hydroxy-trans-3-[2-bis-(trimethylsiloxy)-methylsilanyl-ethyl]-cyclohexyl ester, methacrylic acid trans-2-hydroxy-trans-3-[2-bis-(trimethylsiloxy)methylsilanyl-ethyl]-cyclohexyl ester, and mixtures thereof.

18. The contact lens of claim 13 wherein the siloxane comprises from 40 to 99 weight percent acrylic acid trans-2-hydroxy-trans-5-[2-bis-(trimethylsiloxy)methylsilanyl-ethyl]-cyclohexyl ester and from 1 to 60 weight percent of acrylic acid trans-2-hydroxy-cis-4-[2-bis-(trimethylsiloxy)methylsilanyl-ethyl]-cyclohexyl ester based on the total weight of the two isomers, or from 40 to 99 weight percent methacrylic acid trans-2-hydroxy-trans-5-[2-bis-(trimethylsiloxy)methylsilanyl-ethyl]-cyclohexyl ester and from 1 to 60 weight percent methacrylic acid trans-2-hydroxy-cis-4-[2-bis-(trimethylsiloxy)methylsilanyl-ethyl]-cyclohexyl ester based on the total weight of the two isomers.

19. A coating composition comprising trisiloxane of claim 1.

20. A coating composition comprising copolymer of claim 8.

* * * * *